United States Patent
Irlicht et al.

[19]

[11] Patent Number: 5,991,663
[45] Date of Patent: Nov. 23, 1999

[54] MULTIPLE PULSE STIMULATION

[75] Inventors: Laurence Irlicht, Brighton; Graeme Clark, Eltham, both of Australia

[73] Assignee: The University of Melbourne, Perkville, Australia

[21] Appl. No.: 08/817,481
[22] PCT Filed: Oct. 17, 1995
[86] PCT No.: PCT/AU95/00686
§ 371 Date: Apr. 16, 1997
§ 102(e) Date: Apr. 16, 1997
[87] PCT Pub. No.: WO96/12383
PCT Pub. Date: Apr. 25, 1996
[51] Int. Cl.[6] .............. H04R 25/00; A61F 2/18
[52] U.S. Cl. .............. 607/57; 607/56; 623/10; 623/66
[58] Field of Search .............. 607/65, 56, 57; 623/10, 66; 600/559

[56] References Cited

U.S. PATENT DOCUMENTS

| | | | |
|---|---|---|---|
| 4,408,608 | 10/1983 | Daly et al. | 128/421 |
| 4,593,696 | 6/1986 | Hochmair et al. | 128/419 |

FOREIGN PATENT DOCUMENTS

| | | |
|---|---|---|
| 4681585 | 3/1986 | Australia . |
| 0054418 | 6/1982 | European Pat. Off. . |
| 9103913 | 3/1991 | WIPO . |

*Primary Examiner*—David J. Isabella
*Attorney, Agent, or Firm*—Tiberiu Weisz; Gottlieb, Rackman & Reisman, P.C.

[57] ABSTRACT

A stimulation strategy for cochlear implants is disclosed. The method and devices that provides electrical stimuli seek to approximate the time domain response of a patient's neural system to electrical stimuli, to the time domain response of a normal hearing person to a corresponding acoustic stimulus.

18 Claims, 9 Drawing Sheets

1

MULTIPLE PULSE STIMULATION

TECHNICAL FIELD

The present invention relates to methods and devices for providing electrical stimuli, and a strategy for electrical stimulation, for auditory prostheses such as cochlear implants.

BACKGROUND ART

Cochlear implants of various types have been proposed and constructed. For the purposes of explanation of the present invention, reference will be made to arrangements such as are commercially available from Cochlear Pty Ltd. However, it will be appreciated that the present invention is equally applicable to other types of auditory prostheses. An intracochlear electrode array is surgically implanted in a patient, together with a receiver stimulator unit for providing electrical stimuli to selected electrode pairs within the array. The receiver stimulator unit is connected, via an inductive transcutaneous link or a direct percutaneous connection, to an external sound processing device and microphone.

The present invention is concerned principally with the process of selecting appropriate stimuli, and with the actual stimulus pulses delivered in response to the acoustic stimuli. According to known arrangements, stimuli may be applied between different pairs of electrodes, to provide different modes of stimulation. In general, the electrode pair selected is related to the pitch of a detected tone. In this case, stimuli have generally used a consistent pulse timing and shape, and amplitude is determined by reference to the amplitude of the detected sound signal. It is also known to stimulate at a rate related to a detected tone, so as to induce a pitch percept.

However, it has been determined that the perceptions of patients in response to these stimuli are different from the perceptions using the normal hearing mechanisms. It has been determined that, in particular, the response of the auditory nerve to such stimulation is quite dissimilar to the neural response of a normally hearing person to the same sound.

In a paper by Parkins et al, entitled "A fibre sum modulation code for a cochlear prosthesis", Annals of the New York Academy of Sciences, 1983 at p 490, the authors discuss providing stimuli in such a way as to mimic the neural response of a normal hearing person to acoustic stimuli. The stimulus waveform is modified, using a complex mathematical model, so that the post stimulus time histogram approximates that of the normal hearing case. However, the arrangement described is not suited for real time processing so as to facilitate implementation in an implantable or portable device.

U.S. Pat. No. 4,495,384 to Scott et al discloses a real time processing arrangement for a cochlear implant. This disclosure does not describe a system which accounts for the refractory period of nerve fibres, and as a result the stimuli produced do not provide a neural response having a time domain waveform similar to the normal hearing case.

In a paper by Motz and Rattay, (1988), "Signal processing strategies for electrostimulated ear prostheses based in simulated nerve response", the stimulated authors discuss the problems associated with hyperpolarisation of the auditory nerve fibres, and consequent loss of perception of higher formants by patients. The stimuli were simulated as if presented from a single electrode. The authors propose the use of further pulses after the initial stimulus pulse, the later pulses having considerable linear increases in amplitude, to improve the perception of higher formants. There is no disclosure of selecting pulses so as to produce a desired post-stimulus time histogram in the auditory nerve structures.

It is an object of the present invention to provide a practical arrangement for generating electrical stimuli so that an auditory nerve response is produced which better approximates the time domain response of the neural structures of a normal hearing person to a given acoustic stimulus.

SUMMARY OF INVENTION

According to one aspect the present invention comprises a cochlear implant device, comprising processing means for receiving an electrical signal corresponding to an acoustic signal, and stimulation means adapted to provide electrical stimuli to the cochlea of a human, said stimulation means including an electrode array comprising a plurality of electrodes operatively located within the cochlea, said device being arranged so as to permit selected electrodes to be provided with stimuli, said stimulation means being responsive to control signals received from said processing means, characterised in that said processing means processes said electrical signals in accordance with a predetermined instruction set, said instruction set determining the stimulation to be applied in response to the acoustic signal including the electrodes to be stimulated, the amplitude of the stimuli, and the timing of the stimuli, said processing means providing control signals to said stimulation means to cause said stimulation means to produce a set of stimuli, said set including for at least one electrode a first stimulus pulse and at least one further pulse within the refractory period of at least a substantial number of the nerve fibres stimulated by said first pulse, the set being selected such that the neural structures of a patient in response to said set have a time domain response which is an approximation to the time domain response of a normal hearing person to said acoustic signal.

The instruction set preferably analyses the electrical signal corresponding to the acoustic signal, so as to identify portions of the signal as corresponding to one of a group of predefined features. These may include, for example, phonemes, tones or chords. A look up table may be provided which provides stimulus sets which have been determined to operatively induce an appropriate time domain neural response corresponding to the acoustic feature. Alternatively, the neural response may be directly calculated. This stimulation is then presented via the electrode array.

The sets of stimuli may be selected so as to stimulate selected populations of nerve fibres at different times, so as to take account of the refractory period of the nerve fibres. The sets of stimuli may also take into account the responses of specific nerve fibres, and are preferably tailored to the responses of a particular patient. For example, each patient may have different degrees of array insertion, some electrodes may not be active post-operatively, and different patients have different degrees of nerve survival. The stimulus sets are chosen so as to allow the nerve response to the stimuli to approximate the time domain response of normal hearing patients to the respective acoustic stimulus. This response may be determined with reference to the post stimulus histogram, inter-spike intervals histogram, and/or the period histogram of individual nerves, or of chosen bands or populations of nerve, or by other telemetry from the stimuli.

The stimulus sets may be designed in advance, using preferably a model of neural response and statistical and/or mathematical analysis. Alternatively, the stimulus sets may be calculated in real time. The stimulus sets may be calculated to take into account single unit effects, or population effects, or preferably both. The present invention allows tailoring of the stimuli, both for different acoustic inputs, and for the peculiarities of individual patients. It is believed that the closer the time domain waveform of the evoked auditory response via electrical stimulation can be brought to that experienced by a normal hearing person, the easier it will be for patients to interpret the precepts produced.

BRIEF DESCRIPTION OF DRAWINGS

The invention will be described with reference to the accompanying drawings, in which.

DESCRIPTION

The present invention relates to a broad principle for applying electrical stimuli to patients with acoustic prostheses. It is emphasised that whilst the present invention is described with reference to a specific implementation, a wide variety of possible implementations exist. For example, different models for neural response may be used to estimate the required stimuli, and different stimulation arrangements, for example percutaneous connection, may well be used.

Figure 12:
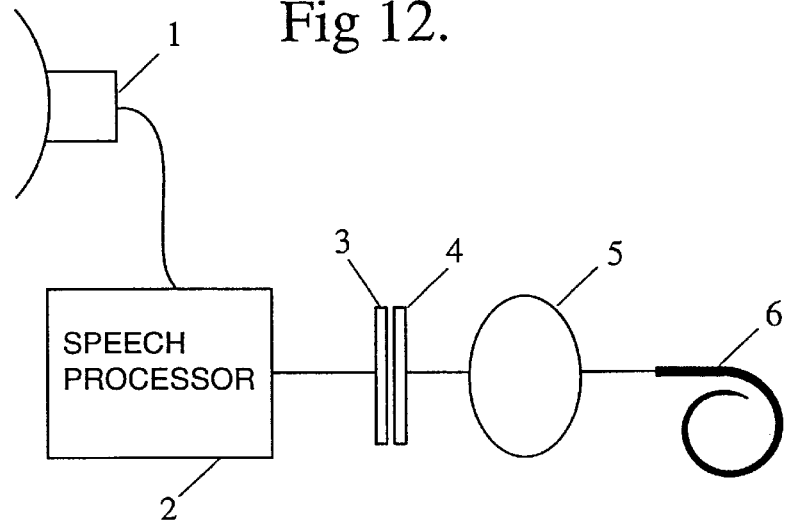
FIG. 12 illustrates schematically a cochlear implant system.

A cochlear implant system of the type contemplated is illustrated in FIG. 12, and comprises in general terms a microphone 1 which receives sound signals and passes a corresponding signal to the speech processor 2. The speech processor processes the received electrical signal to produce a set of stimulus data. This is transmitted, together with power, from the external coil 3 to internal coil 4, and then to the receiver stimulator unit (RSU) 5, which then provides stimulus pulses to the selected electrode pairs of electrode array 6 so as to stimulate the nerve fibres and provide a percept of sound to the user.

The neural response cannot be derived as a trivial function of, say, the input sound signal. One aspect of the difficulty of accurately simulating the response relates to the complexity of the system. The normal hearing ear has approximately 30, 000 nerve fibres, each of which can reach action potential independently of the others at any time during the stimulus. It is not possible to generate electrical pulses which cause this system to behave identically to the normal hearing situation.

One aspect of the implementation of the present invention relates to varying the numbers, amplitude, shape and rate of the pulses to evoke an approximation of the NHNR. This is achieved in particular by evoking the correct number of action potentials (counted across either one representative fibre, or alternatively across the population of fibres) within each "phase" of the waveform, or averaged over many appropriately chosen phases of the waveform. This phase corresponds to the available divisions within the stimulation period, which is limited by the modulation rate—if the modulation rate was 4 times the frequency of a tone, then each "phase" would be one quadrant of the waveform. This results in a "staircase" approximation to the NHNR which is very similar to that of the acoustical case. The specially designed stimuli are applied across each period of the simulated tone, and are designed via computer simulation, and mathematical analysis, of the auditory nerve's response to both auditory and electrical stimulation.

Modifications to the waveform are used to improve the spatio-temporal neural response. These modifications include (but are not limited to) modifications to the number, amplitude, spacing, and width of the pulses to better simulate the spatio-temporal pattern of the NHNR. These degrees of freedom are provided in conventional systems, but are generally not exploited.

The present invention allows for various types of temporal response to be induced, as is required in various applications. One approach is to utilise the present invention to evoke as near an approximation as possible to the correct population per stimulus time histogram, by applying several pulses per stimulus period. The pulse amplitudes may be chosen so as to generate the correct number of action potentials in each part of the waveform. The pulse sizes may be chosen using various means, examples of which are discussed below.

A further aspect of the present invention is that by utilising the refractive properties of neurons, it is possible according to the present invention to provide stimuli such that different bands within the stimulation range of an electrode (SRE) fire at different times. This allows for the stimuli to evoke desired inter-pulse timings within each band, so that the phase relationship between the bands in normal hearing can be approximated. The size of the bands chosen may be selected, so that the band size may be selected to be that size which provides the best percepts for the patient. This may be customised for each patient.

The present invention is described largely in the context of available implant systems, which utilise a standard biphasic pulse. Altering the pulse shape will necessarily alter the time domain response of the associated neural structures. The present invention is not limited in scope to the use of existing or standard pulse shapes, although clearly alternative pulse shapes will alter the details of the effects noted above.

In order to more fully understand the present invention, we will initially briefly consider its theoretical basis. In a conventional cochlear implant, the neurones of the auditory nerve are stimulated by application of a series of biphasic currents between electrodes of the electrode array. Each biphasic stimulation causes a group of neurones to fire. The number of neurones that fire due to a stimulation is determined by such factors as relative location of the group of neurones to the stimulating electrodes, and the history of stimulation of those neurones. If many of the neurones are in a refractory period due to past stimulation then the application of new stimulation will not cause as many of them to fire as would be the case if they were being stimulated for the first time.

Figure 1:
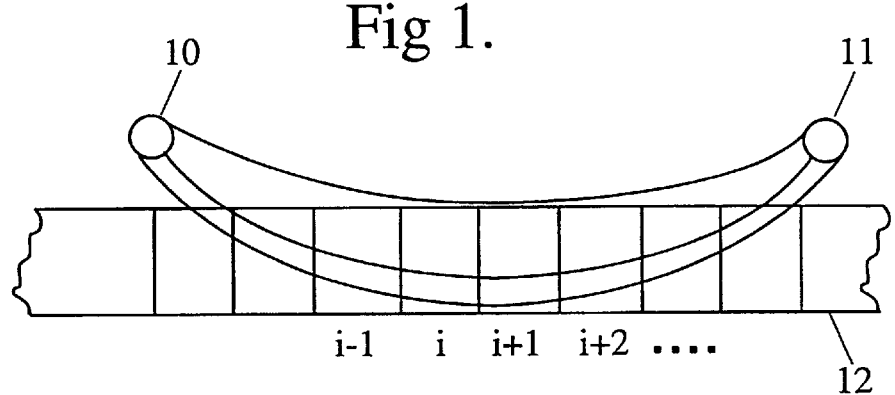
FIG. 1 illustrates schematically an aspect of the theoretical basis fro the present invention.

It is further desirable according to the present invention to provide an estimate which is representative of the temporal response of the wider population of nerves, not merely those close to a single electrode. In order to overcome variations in neuron response due to location with respect to the stimulating electrodes, the neurones can be considered as divided into strips, each of which are assumed to contain neurones that are equally stimulated by the application of a given stimulus pulse. This is illustrated schematically in FIG. 1. Neurones 12 in the region of electrodes 10, 11 are notionally divided into strips, labelled i, i+1, and so forth.

Suppose that a single biphasic stimulation is applied between electrodes 10,11, at various amplitudes, and the ith strip of neurones monitored. Whilst of course in practise any given pulse will stimulate multiple strips, it is assumed that this strip contains the neurones most responsive to the stimulating electrode. The stimulus function $S_k$ describes the neural response from the kth pulse. $A_k$ is the amplitude of the kth pulse. It is possible to make up a table for each strip relating $A_k$ to $S_k$.

In practice the neurones are not stimulated by isolated biphasic pulses but by a series of stimulations. Each electrical stimulation will elicit a neuronal response from a single strip of neurones of $Nl_k$ action potentials, where N is the number of neurons in that strip, and $l_k$ is the averaged probability of any neuron from that strip acheiving action potential during pulse k. It is known that the pulse in a series of stimulation pulses that elicits $l_k$ has the same amplitude as the isolated pulse that elicits $S_k$ where $S_k$ and $I_k$ are related by:

$$S_k \approx l_k / \left[ 1 - \sum_{w=k-(n+c)}^{k-1} l_w \gamma(k-w) \right]$$

Let the pulse period equal T. (n+c) is the length of the relative refractory period divided by T,, and $\gamma(k-i)$ is one minus the refractory function measured for time kT since the last action potential.

Therefore it is possible to generate a particular $l_k$ by determining $S_k$ and then looking up the appropriate amplitude of the biphasic pulse $A_k$ to be applied.

So far it has been shown how to determine the amplitude of the biphasic stimulation to be applied in order to elicit a desired neural response $I_k$ in the ith stimulated strip of nervous tissue.

Linking of Acoustic Signals to Neural Response

Current speech processors used in cochlear implant technology rely on extracting significant features of speech. For example, using the SMSP process, electrical signals corresponding to received sound signals are processed by means of band pass filters, eg. 16, to provide a signal corresponding to amplitude in each channels. A selected number of said amplitude signals having the greatest amplitude, e.g.6, are used to modulate the amplitude of the stimulation pulse.

In order to incorporate the present invention into such a system it is necessary to calculate the $l_k$ which would arise in the normal hearing situation in each band where stimulation is to occur. This $l_k$ may be calculated by use of an approximate model of the cochlea and normal neuronal response. See for example Parkins et al "A Fibre Sum Modulation Code for a Cochlear Prosthesis", Annals of the New York Academy of Sciences, 1983 p490, or one of the many other published models.

Figure 2:
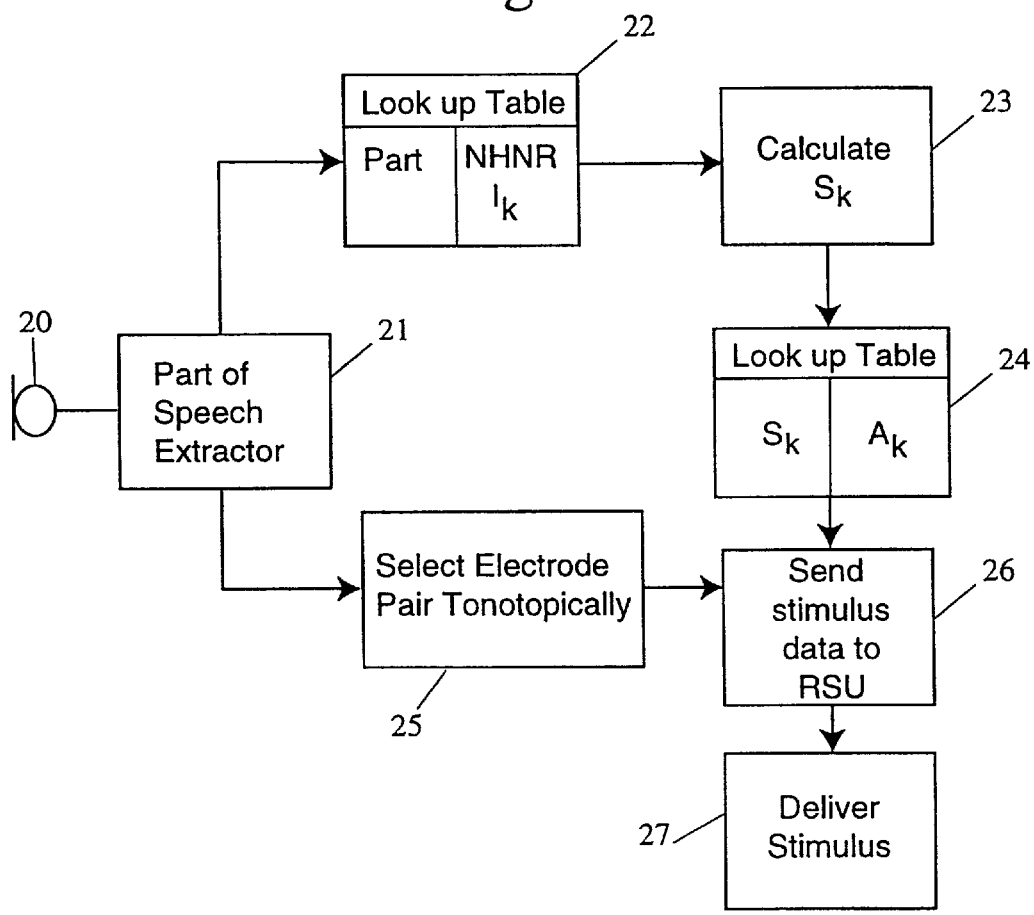
FIG. 2 illustrates in block form processing according to the present invention.

The $l_k$ is then mapped to the appropriate $S_k$ by means of the equation above, and the map of $A_k$ to $S_k$ is used in order to determine the amplitude of the biphasic pulse to be applied. This process is described in FIG. 2. An input signal 20 is processed by software 21 in order to extract a particular feature or set of features. This process may be a conventional cochlear implant type, for example SMSP or identification of formants. Alternatively, it may be a software process to recognise phonemes or similar features, such as discrete musical tones. The recognised feature is referenced via look-up table 22 to provide a desired normal hearing neural response, $l_k$, which corresponds to a percept of the feature extracted. $S_k$ can then be determined with reference to the equation above. An amplitude $A_k$ for each pulse can then be derived from look-up table 24. Simultaneously, according to this implementation, the input signal 20 is processed 25 so as to select an electrode pair for tonotopic stimulation. The stimulus is then determined 26 by combining the derived $A_k$ with the electrode site selected at 25, to provide a set of stimuli to electrode array 27.

The look up table may be provided using any conventional memory device. The first table stores the required type of patient percept, that is, the feature extracted ( e.g. a phoneme, or a tone), with corresponding normal hearing neural response patterns. The other input to the table is the required volume level of the perception. The output of the lookup table is a set of electrical stimuli which evoke the desired neural response. These are preferably calculated off-line via methods similar to those described above, and stored. This arrangement allows for a reduction in processor capacity, as it is not necessary for whole waveforms to be fully calculated.

The second lookup table 24 requires as input the width of the stimulation pulses, the rate of stimulation, and the desired stimulus function ($S_k$), and returns the amplitude $A_k$ of the stimulus required for this. The values for the lookup table may be obtained in a variety of ways . One approach is to use animal studies with a variety of pulse rates at a variety of amplitudes and rates (for each pulse width). From the responses measured, the 's' function can be calculated.

Figure 3:
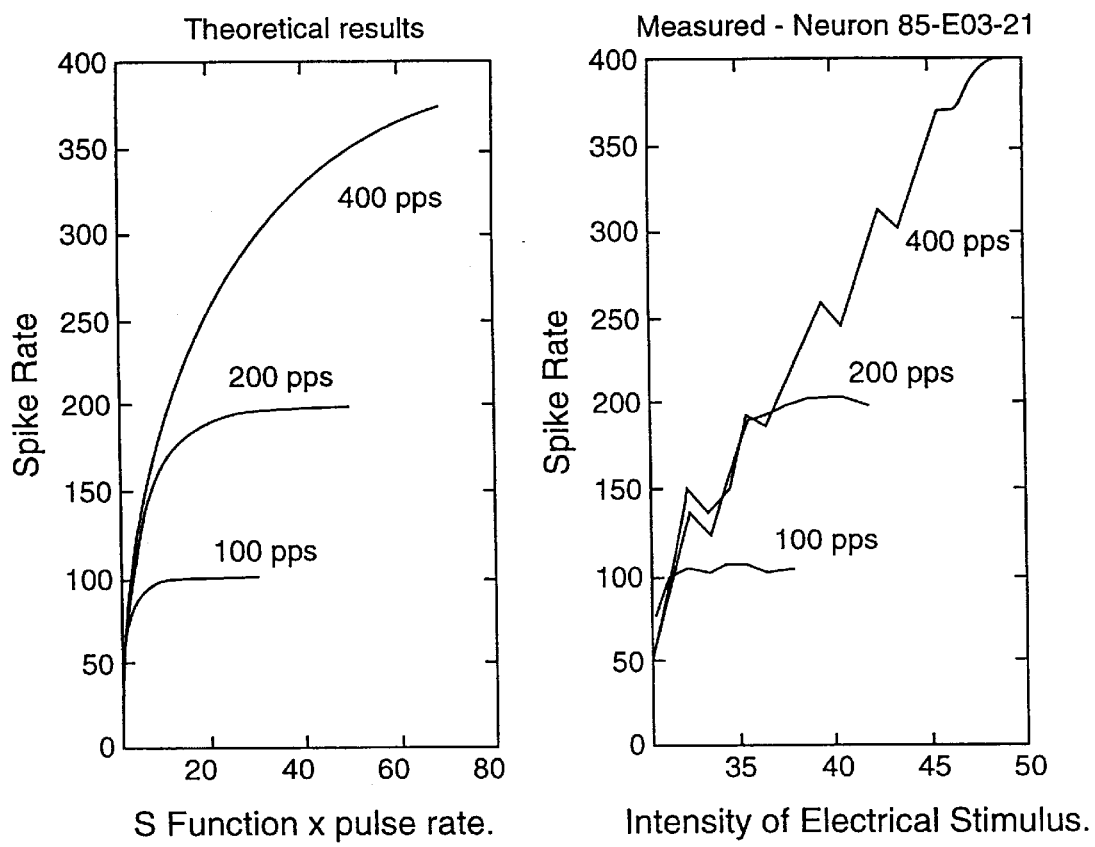
FIG. 3 illustrates graphically theoretical and measured plots of spike rate against stimulus function.

FIG. 3 lists the expected spike rates for biphasic pulses as a function of the S function (for given pulse rates and pulse width) versus the actual experimental results. The experimental results were obtained by putting in fixed width biphasic pulses at various pulse rates and intensities, and graphing the neural response rates. The theoretical values may be calculated as follows.

Assume the stochastic process describing the timing of the action potentials is a self exciting point process (Snyder and Miller, 1991). Define the number of spikes (events) to time t as Nt, then at any time t, the time since the last spike equals $t-t_{Nt}$. The intensity of the point process (Snyder and Miller, 1991) is equal to s(t) $r(t-t_{Nt})$, where $s(t) \geq 0$ is a stimulus related function, depending on time (determined by the properties of the neuron and also the signal presented to the neuron) and r (.)≧0 is a refractory function, which lowers the rate of action potential generation as a function of the time since last action potential. r(.) is determined solely by the properties of the neuron, and possibly also by the type of stimulus (electric or acoustic), and is independent of the size of the stimulus.

Consider a system where the s function is a set of identical pulses spaced at a period of T with the width of each pulse W being less than the dead time of the neuron. Let the refractory function r (t–$t_{Nt}$) be constant over the following regions:

$$r(t - t_{N_t}) = \begin{cases} 0, 0 \le (t - t_{N_t}) \le w \\ \alpha_n, nT - w \le (t - t_{N_t}) \le nT + w, 1 \le n \le (b-w)/T \\ 1, (t - t_{N_t}) \ge b \end{cases}$$

Define $$A = e^{-\int_0^w s(\tau)d\tau}$$

A is the probability of there being no points assuming a Poisson rate of s (t) during the pulse, and no refractory effects. $\alpha_n$ is the size of the refractive function, where the last action potential occurred n pulses ago. Define N as the smallest integer such that (N+1)T–W≧b. Then, the steady state average rate of neural firing equals:

$$R = \frac{(1-A)}{T\left(1 + \sum_{n=1}^{N}[1 - A^{1-\alpha_n}]A^{\sum_{j=1}^{n}\alpha_n}\right)}$$

The values for lookup tables which relate the S function to the electrical intensity, for given conditions, may then be derived. This may be done in a number of ways.

A relatively simple method involves simply measuring the 'S' function directly for a given pulse set up by measuring the neural response under a number of conditions of pulse rate and intensity.

For instance, from FIG. 3, a pulse at an intensity of about 35 when presented at 200 pps would equate to an S function of about 10, and increases in intensity will approximately relate to increases in S function in a linear plus offset relationship.

Alternatively, at 200 pps, to produce an S function of, say 20, a stimulus intensity of about 40 is required.

Of course, further research may result in a more detailed representation of the relationship, but this simple initial approach provides a reasonable representation.

An alternate method of determination of the necessary current values for a given pulse rate and width would be to (with each patient) apply a series of pulses at fixed rate and width, and determine the threshold and comfortable levels of current. Then, a second parameter which indicates the size of the effective 'S' function at each level could be determined either by masking studies, or alternately by experiments where such a parameter is changed, and the perceptual response noted, ie. a particular sound could be coded, and then repeatedly played to the patient, under the assumption of a given proportionality between the current intensity, and the S function. The proportionality which returns the 'best' response—either in terms of naturalness or in terms of signal discriminability, could be stored in the look up table.

Thus, in this particular implementation, there would be three parameters: a threshold and comfortable level current, and a scalar parameter relating the current intensity (at a given pulse rate) to size of the 'S' function. Note that this would need to be done for each electrode stimulation combination. (ie. monopolar on each, bipolar on each pair, etc).

It will be appreciated that the pulse timing may be determined in various ways, within the scope of the present invention. In a simple implementation, a constant pulse rate may be used for all electrodes. This rate must of course be much faster than the relative refractive period, typically 20 ms, and is preferably less than 1 ms. A preferred implementation uses a pulse rate for each electrode such that the rate is an integral multiple of the characteristic frequency of the adjacent neural population.

Figure 10:
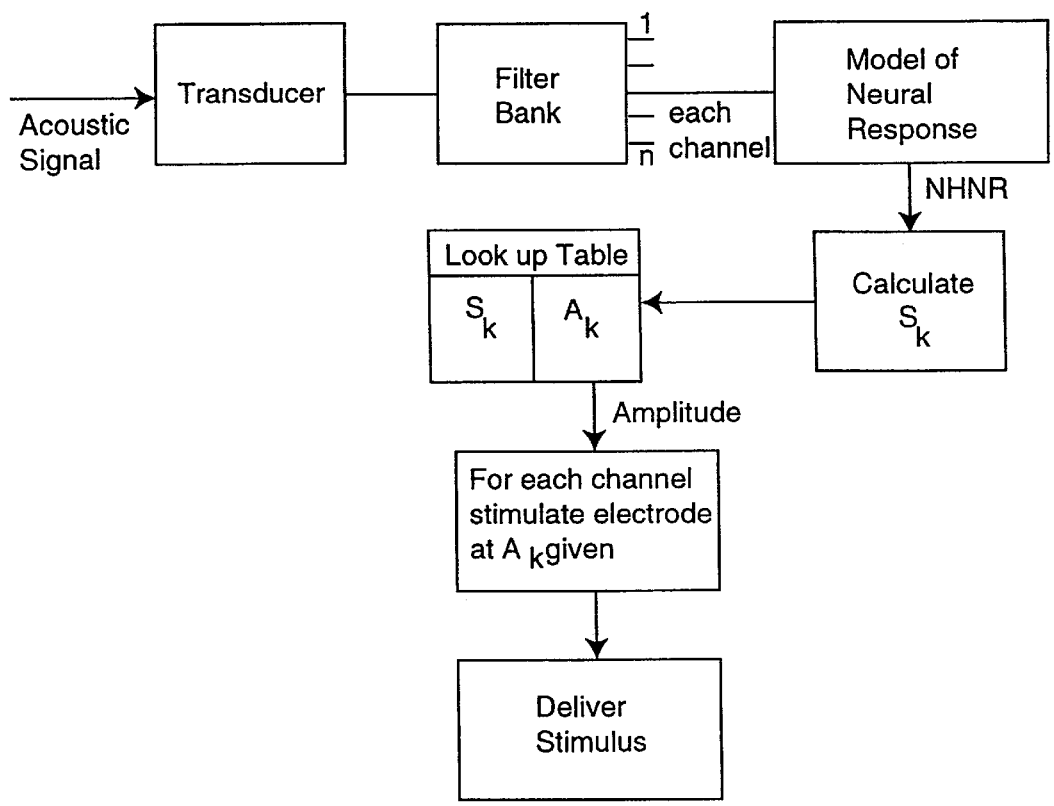
FIGS. 10 and 11 illustrate further implementation of the present invention in block form.

FIG. 10 illustrates in block form an alternative implementation of the present invention. In this case, the received acoustic signal is processed by a transducer, and then enters a filter bank with n outputs. Illustratively, this may be 6. For each channel, a model of neural response for that part of the neural structure is used to produce a normal hearing neural response (NHNR) for that part of the acoustic signal falling within the channel. The $S_k$ can then be calculated using the equation shown above. The $S_k$ can be related to $A_k$ in a look-up table, as previously discussed. This $A_k$ can then be used as the basis for an instruction to the RSU to stimulate the appropriate electrode pair at amplitude $A_k$.

Figure 11:
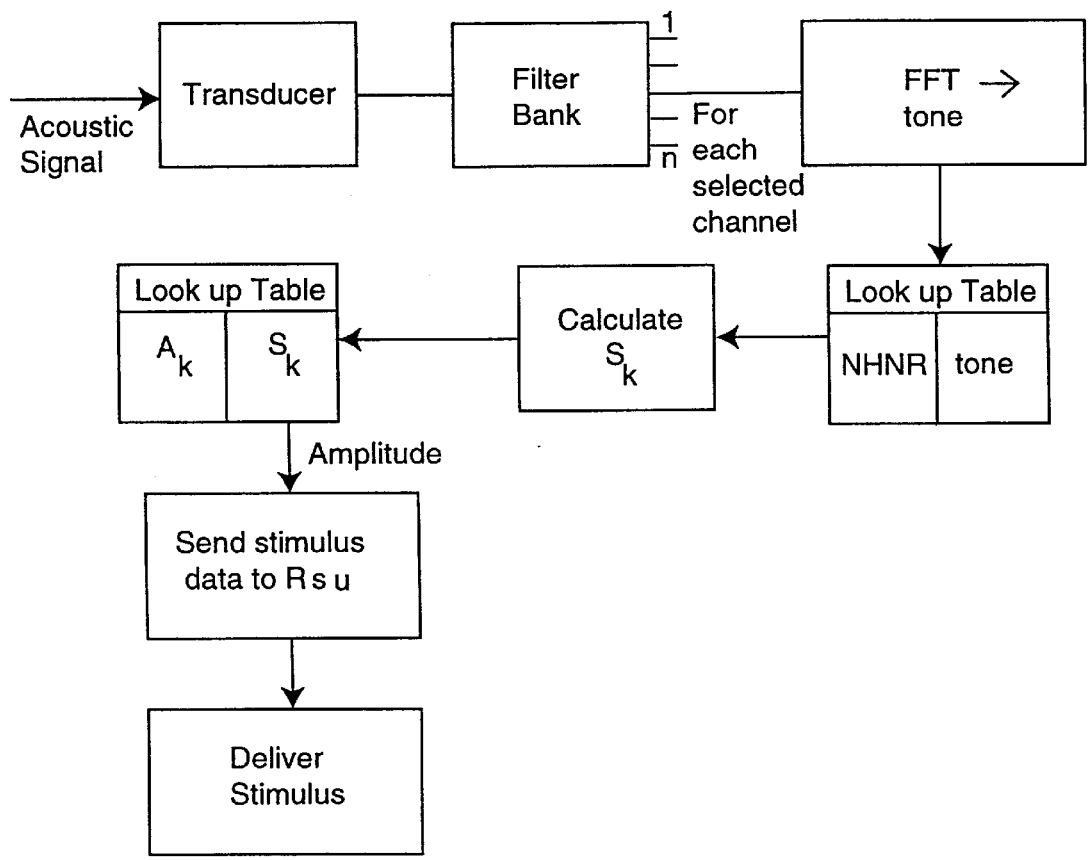

FIG. 11 illustrates a related implementation to FIG. 10. The distinction is that for each channel output from the filter bank, FFT techniques are used to derive a fundamental tone. Using a similar process to that described in relation to FIG. 1, this tone is related to a NHNR via a look up table, the $S_k$ calculated, and the corresponding $A_k$ determined from a further look-up table. A stimulus instruction is then sent to the RSU based on the determined $A_k$, and the electrode site corresponding to the tone. This process may be performed for each channel, or for a selected set of channels, determined via the SMSP technique, which have the greatest amplitude.

Figure 8:
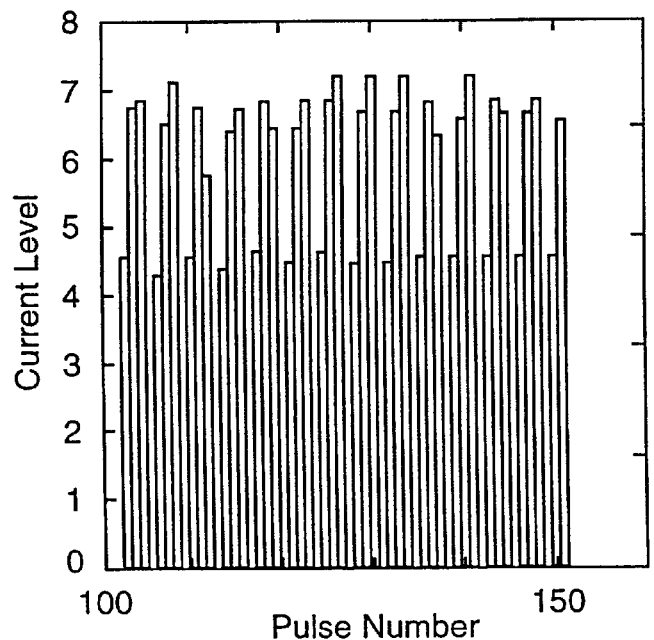
FIG. 8 illustrates current levels required to produce the output of FIG. 5.
Figure 9:
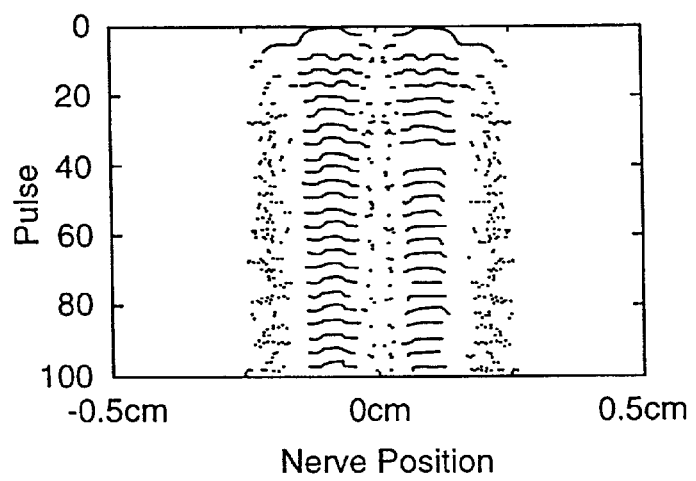
FIG. 9 illustrates the spread of action potentials excited by the stimulation.

FIGS. 8 and 9 illustrate the principle of the present invention. To cause a population response similar to that from a NHNR for a 1 kHz tone, we could apply a continuously repeating set of four μs biphasic pulses, where the amplitudes were in the ratio of 4,6.5,7,0, resulting in a neural response in the ratio of 10,24,10,0. This is illustrated in FIGS. 8 and 9.

The stimulation strategy proposed according to the illustrative example below is designed to be capable of implementation on a speech processor for cochlear implants which codes signals in terms of biphasic pulses. The examples illustrated utilise a fixed-width biphasic—bi-polar pulse, with an overall pulse width of 250 us.

Figure 4:
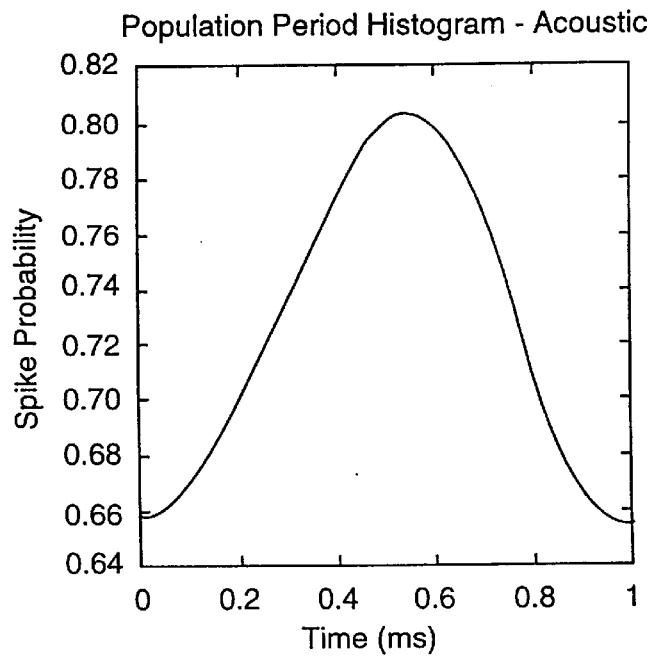
FIG. 4 illustrates a sample period histogram of a population of nerves.
Figure 5:
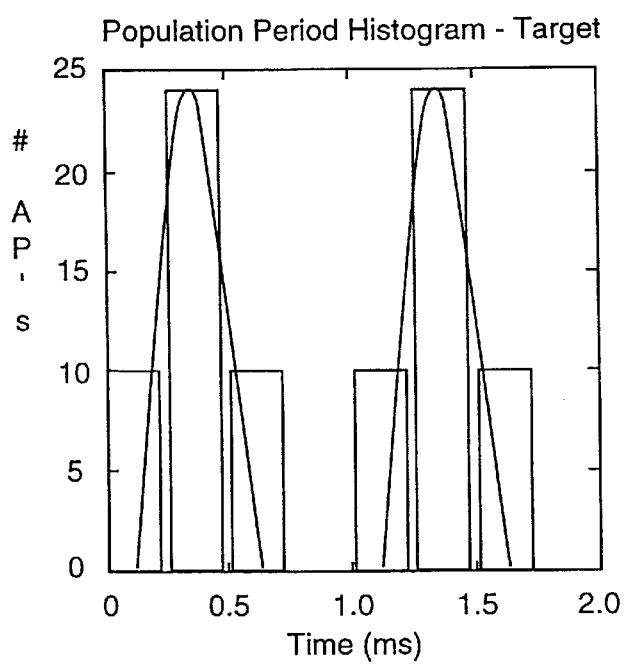
FIG. 5 illustrates a multiple pulse histogram according to one embodiment of the present invention.

FIG. 4 illustrates a population histogram for a population of 64 nerves around the 1 KHz place in a cat cochlea of total length 2.5 cm. The acoustic input is a 1 KHz tone. FIG. 5 illustrates an approximation using multiple pulses according to the present invention.

Figure 6:
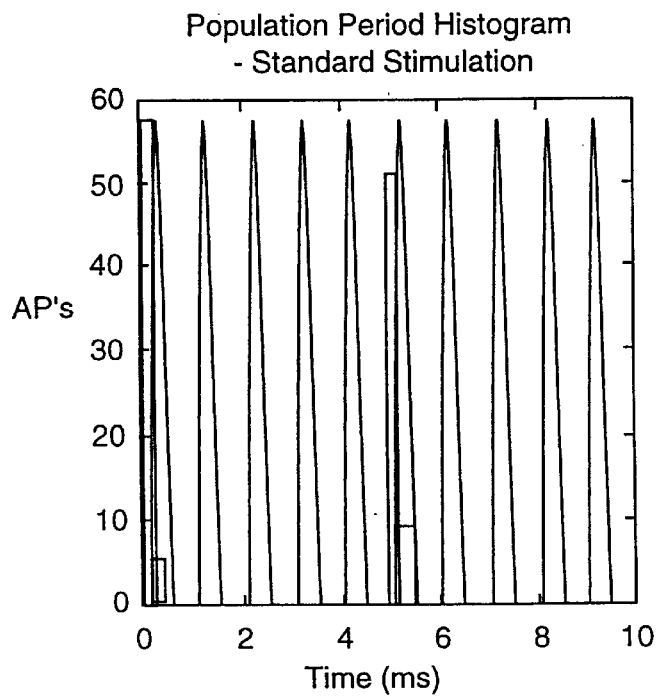
FIG. 6 illustrates a histogram produced according to standard techniques.

FIG. 6 illustrates output pulses using one pulse per period, in other words, using standard stimulation techniques. It is clear that such fixed-rate stimulation techniques can not form a close approximation to the desired output histogram at any frequency other than that of stimulation.

Figure 7:
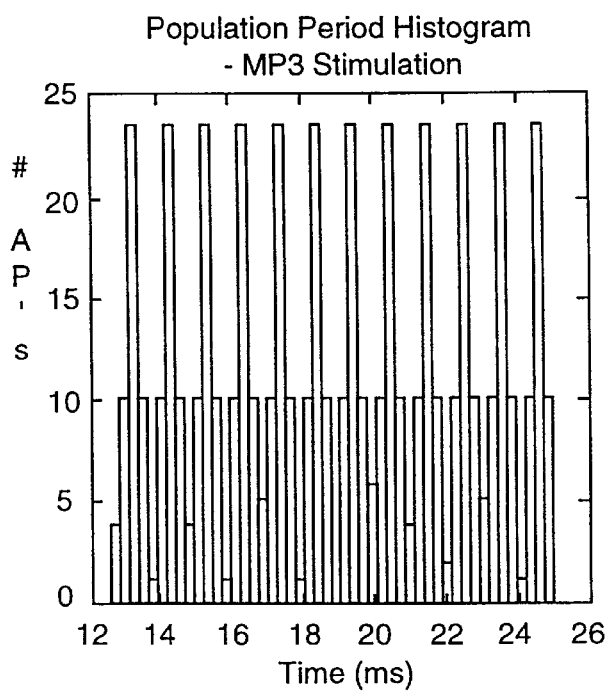
FIG. 7 illustrates a histogram according to an embodiment of the present invention.

A multiple-pulse electrical stimulation model was iterated in a trial and error fashion until a set of current levels was found which provided the required histogram according to the present invention. The results can be seen in FIG. 7. It is clear that for each period, the actual histogram closely resembles the desired approximation of FIG. 5. Clearly, when compared to FIG. 6, the present invention provides a much closer approximation.

EXAMPLE

The following describes the implementation of the inventive techniques in relation to a specific sound input.

Figure 13:
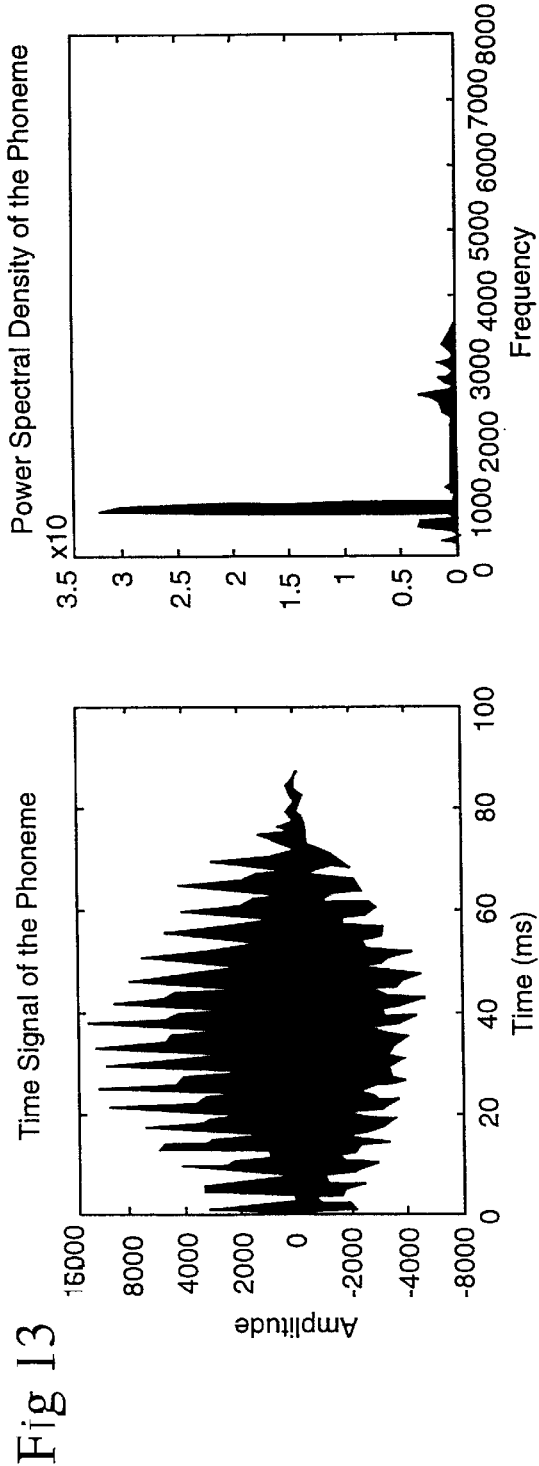
FIG. 13 illustrates the time and power signals associated with a phoneme.

The phoneme /e (sounds like a short 'eh') is shown in FIG. 13, together with its power spectral density. Note that the spectrum has a number of peaks in the frequency spectrum (at about 800, 500, and 200 Hz). These may be used as the main frequencies targeted for stimulation. The signal is from an isolated sound.

It was applied to the model from Benjamin D Brayant and John D Gowdy, "Stimulation of Stages I and II of Seneff's Auditory Model (SAM) Using Matlab", published in the proceedings of the 1993 Matlab User's Group Conference.

Figure 14:
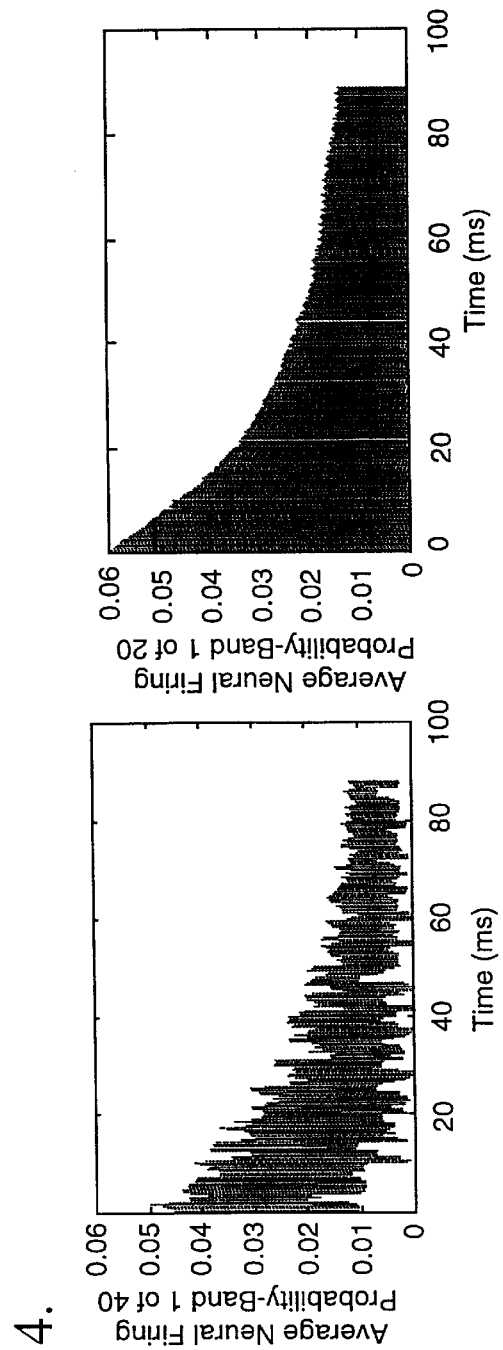
FIG. 14 illustrates firing probabilities for various bands of neurons.

The model provides the averaged neural response for neurons from forty regions of the basilar membrane (ranging in characteristic frequency from high frequency to low frequency). Of course, the model could be set for any number of bands required, for example, the response of bands corresponding to each stimulating electrode. The response of some of the bands are shown as FIG. 14. It will be appreciated that other models and software could be used to produce this result.

The inventive technique may be used to code each band which corresponds to the characteristic frequency of neurons close to an electrode. For now, let us imagine that band 40 (for instance) corresponded to an electrode, and examine how the inventive technique could be used to generate pulses for that electrode. It will be appreciated that other electrodes would also be coded at the same time.

In the neural response here, there are two aspects. A broad lowering of probability over time, probably due to onset effects, as well as a fine structure. The present invention provides information to the user about both.

The fine structure of response here has approximately 20 periods in the 80 ms, corresponding to a period of 4 ms, or a frequency of 250 hz. As an example, we will code with 8 pulses per period, requiring a coding frequency of 2000 Hz, or in other words a bin size of 0.5 ms.

The probabilities shown in the graph will be the $l_k$, or NHNR, of the theory above. So using the formulas given, it is possible to work out the $S_k$ which will, give the required responses.

Let us assume that the population of neurons we wish to control can be approximated by 3 approximately equally stimulateable regions (the centre one being the most stimulateable), and we want the total number of action potentials from this summed population (divided by the total number of neurons in the summed population) to follow the curve of the Figure.

Figure 15:
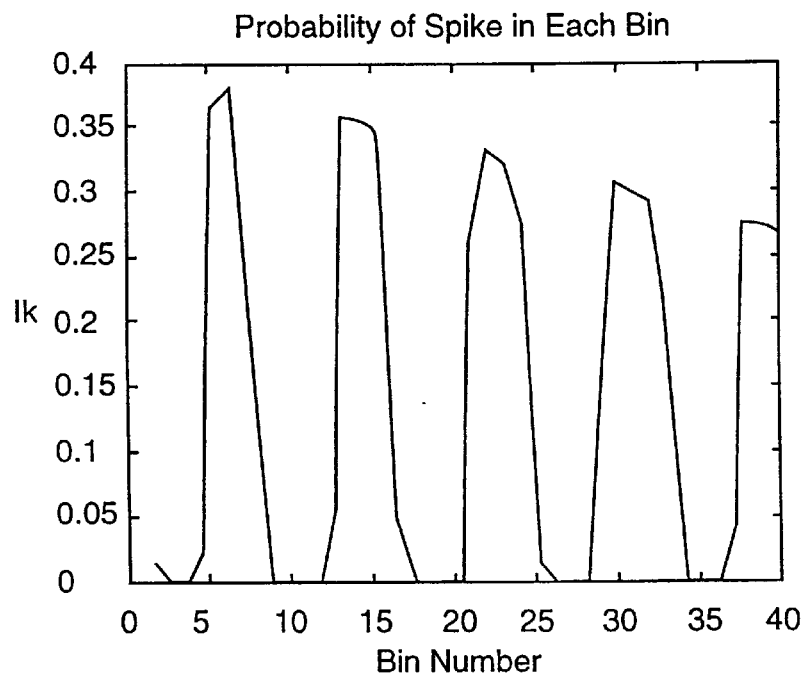
FIG. 15 illustrates the probability of spikes in various time periods for a particular selected band.

Use the following equation, $$S_{k,i} \approx l_{k,i} / \left[ 1 - \sum_{k-(n+c)}^{k-1} l_{w,i} \gamma(k-w) \right]$$

$$\approx l_{k,i} / G_{k,i}$$

where $S_{k,i}$ is the stimulation function for the ith region during pulse k, $l_{k,i}$ is the averaging probability of neural response for the ith region during pulse k, and $\gamma(k)$ equals one minus the refractory function evaluated for the case where the last action potential occurred k.T ago The probability of firing in each 0.5 ms bin, can then be calculated, as shown in FIG. 15.

From this calculation, the probabilities required for the first 10 bins are:

| k | $l_k$ |
|---|---|
| 1 | .014 |
| 2 | .000 |
| 3 | .000 |
| 4 | .022 |
| 5 | .371 |
| 6 | .382 |
| 7 | .231 |
| 8 | .001 |
| 9 | .000 |
| 10 | .000 |

A given electrical pulse will elicit different responses at different distances from the site of stimulation. $\alpha_i$ is defined as the ration between a nominal S for some pulse, and the actual S generated for the ith region. Let us assume that the $\alpha_i$ for the three sub-populations are 0.7, 1 and 0.7 for each population (1, 2, 3).

Figure 16:
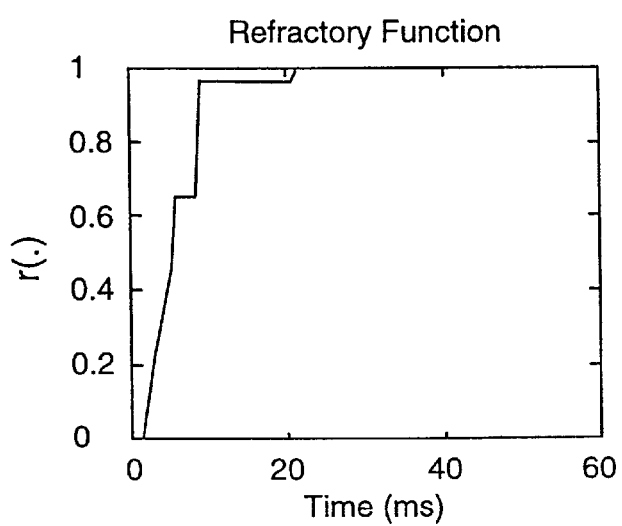
FIG. 16 illustrates a sample refractory function.

FIG. 16 gives approximate values of the refractory function$(1-\gamma)$, and the gammas would be (very approximately), about 1 for the first three bins (1 ms), and decreasing from there to about zero after about 25 ms (the 50th) bin. Therefore, responses from the last 50 bins are relevant when calculating the response in any bin.

So gamma will be approximately 1 for the first two bins, and 0.5 after bin 10 or so, and then 0.97 after bin 45, etc.

To obtain the required population per-stimulus time histogram from the total of the 3 sub-regions, we apply the formula:

$$S_k \approx \frac{l_k}{\sum_i [G_{k,i} \alpha_i]}$$

So, to do the calculation:
1. Assume that before time 0 there has been no significant amount of firing. (If a previous token was coded earlier, then the processor will remember the $l_k$'s from that token, and how long ago).
2. Loop over each pulse, or 'k'.
3. Calculate $G_{k,i}$ as described above.
4. Using the equation above, calculate the required $S_k$. Also, store the three $l_{k,i}$ values this will evoke for use in calculations of future $G_{k,i}$ values.
5. Using the lookup table (as previously discussed) determine the required intensity of the pulse.
6. Administer the pulse for the correct amount of time, and go to step 2.

This procedure is readily implementable using conventional software techniques.

Variations and alternatives are possible within the general scope of this invention, as will be apparent to the reader. In particular, it is noted that the various processing components may be differently arranged, so that for example some or all the look up tables are located within the implanted portion of the device.

We claim:
1. An auditory prosthesis, comprising:
   processing means for receiving an electrical signal corresponding to an acoustic signal, and
   stimulation means adapted to provide electrical stimuli to the cochlea of a human, said stimulation means including an electrode array having a plurality of electrodes operatively located within the cochlea,
   said prosthesis being arranged so as to permit selected electrodes to be provided with stimuli, said stimulation means being responsive to control signals received from said processing means, wherein said processing means processes said electrical signals in accordance with a predetermined instruction set, said instruction set determining the stimulation to be applied in response to the acoustic signal including the electrodes to be stimulated, the amplitude of the stimuli, and the timing of the stimuli, said processing means providing control signals to said stimulation means to cause said stimulation means to produce a set of stimuli, said set including for at least one electrode a first stimulus pulse and at least one further pulse within the relative refractory period of at least a substantial number of the nerve fibres stimulated by said first pulse, the set being selected by said processing means to induce in the neural structures of a patient a time domain response which is approximates the time domain response of a normal hearing person to said acoustic signal.

2. An auditory prosthesis according to claim 1, wherein said processing means includes means for analyzing said electrical signal and determining which of a predefined group of acoustic features a portion of the electrical signal corresponds to, and a look-up table referencing acoustic features of said group to control signals corresponding to sets of stimuli;

wherein said processing means is adapted to transmit said control signals to said stimulation means to generate sets of stimuli for said electrodes.

3. An auditory prosthesis according to claim 1 or claim 2, wherein the neural structures of the patient include populations of nerve fibres, each population of nerve fibre being most responsive to a particular frequency range and having a characteristic response in the time domain, and wherein said processing means is adapted to analyze said electrical signal by designating a plurality of frequency channels, each channel corresponding to one of said populations, and for each channel said processing means is adapted to perform a separate analysis to determine said control signals.

4. An auditory prosthesis according to claim 1, wherein said processing means includes a memory storing a model of meural responses of normal persons with normal hearing and is adapted to process the received acoustic signal using said model to determine an ampplitude of said set of stimuli.

5. An auditory prosthesis according to claim 4, wherein processing means is adapted to determine said amplitude by calculating a desired stimulus function for the patient corresponding to the approximation of the time domain response of a normal hearing person, and thereby deriving said amplitude from said stimulus function.

6. An auditory prosthesis according to claim 4, wherein said processing means includes a look-up table relating said stimulus function to said amplitude and wherein said processing means determines said amplitude from said loop-up table.

7. An auditory prosthesis according to claim 1, wherein for each stimulated electrode, the stimulus set comprises multiple pulses presented at a rate faster than the relative refractory period of the associated neurons.

8. An auditory prosthesis according to claim 7, wherein said processing means includes a memory for storing a population per-stimulus time histogram for adjacent neurons adapted to select the stimulus set for each electrode such that the adjacent neurons exhibit in response to said stimulus set said time histogram which is an approximation to the population perstimulus time histogram generated by a corresponding acoustic stimulus in a normal hearing person.

9. An auditory prosthesis according to claim 8, wherein said processing means further comprises a second memory for storing at least one of a model response, patient response data and telemtery information from the patient, and wherein said processing means is adapted to select said instruction set for stimuli for each stimulating electrode in accordance with one or more selected from the set comprising a model of neural response, predetermined patient response data, and telemetry from said stimulating means.

10. An auditory prosthesis according to claim 7, wherein said processing means is adapted to select several sets of stimulation signals, each set being chosen so as to excite different population bands of neurons.

11. An auditory prosthesis according to claim 10, wherein said processing means is adapted to select a size of a poplulation band in accordance with experimentally derived patient data in order to maximize the naturalness of the perception of sound by patients.

12. An auditory prosthesis according to claim 11 further comprising means for setting characteristics of the patient, and wherein said processing means is adapted to set said size of the population bands based on said characteristics.

13. An auditory prosthesis comprising:

a sensor that senses ambient sounds and generates a corresponding electrical signal;

a signal processor coupled to said processing means for receiving an electrical signal and generating in response stimulation signals;

an array of electrodes means adapted to receive said stimulation signals and apply said stimulation signals to the neurons of a patient, provide electrical stimuli to the cochlea of a human, said stimulation means including an electrode array having a plurality of electrodes operatively located within the cochlea;

wherein said signal processor includes a memory storing information indicative of the normal neural response characteristic of normal patients, said signal processor including a stimulation signal selector adapted to select said stimulation signals which approximate in the patient the neural response of normal persons based on said information.

14. The prosthesis of claim 13 wherein the patient has neurons characterized by a refractory period, and wherein said signal processor generates a first stimulation signal corresponding to said electrical signal and a second stimulation signal within said refractory period resulting from said first stimulation signal, said second stimulation signal being selected by said signal processor based on the normal neural response.

15. The prosthesis of claim 13 wherein the normal neural response includes a time domain response and wherein said signal processor is adapted to select said stimulation signals based on said time domain response.

16. The prosthesis of claim 1 wherein said signal processor includes a feature extraction element coupled to said electrical signal to detect a plurality features of said electrical signal, and wherein said signal processor generates one of a set of stimulation signals, each set corresponding to one of said features.

17. The prosthesis of claim 16 wherein said signal processor includes a look-up table, said look-up table being arranged to reference features of said electrical signals with corresponding stimulation sets.

18. The prosthesis of claim 1 wherein signal processor is adapted to designate a plurality of frequency channels, each stimulation set being assigned to one of said channels, said frequency channels being activated in response to a frequency content of said electrical signals.

* * * * *